(12) United States Patent
Lee et al.

(10) Patent No.: US 11,009,503 B2
(45) Date of Patent: May 18, 2021

(54) BIOCHEMICAL DETECTION DEVICE WITH CONTROLLED REACTION INCUBATION TIME AND METHOD FOR PRODUCING THE SAME

(71) Applicant: Research & Business Foundation Sungkyunkwan University, Suwon-si (KR)

(72) Inventors: Nae Eung Lee, Suwon-si (KR); Won Il Lee, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 302 days.

(21) Appl. No.: 16/276,795

(22) Filed: Feb. 15, 2019

(65) Prior Publication Data

US 2019/0265234 A1  Aug. 29, 2019

(30) Foreign Application Priority Data

Feb. 26, 2018 (KR) .......................... 10-2018-0022635

(51) Int. Cl.
| | |
|---|---|
| *B01L 3/00* | (2006.01) |
| *G01N 33/537* | (2006.01) |
| *C12M 3/06* | (2006.01) |
| *G01N 33/53* | (2006.01) |
| *G01N 33/543* | (2006.01) |
| *G01N 33/50* | (2006.01) |
| *G01N 33/00* | (2006.01) |

(52) U.S. Cl.
CPC .... *G01N 33/5375* (2013.01); *B01L 3/502715* (2013.01); *B01L 3/502738* (2013.01); *B01L 3/502753* (2013.01); *B01L 3/502769* (2013.01); *C12M 23/16* (2013.01); *G01N 33/5302* (2013.01); *G01N 33/54366* (2013.01); *B01L 2400/0677* (2013.01); *G01N 2033/0096* (2013.01)

(58) Field of Classification Search
CPC .. B01L 3/502715; B01L 3/5027; B01L 3/502; B01L 3/50; G01N 33/5375; G01N 33/537; G01N 33/536; G01N 33/53; G01N 33/50
USPC ................................ 422/412, 408, 401, 400
See application file for complete search history.

(56) References Cited

U.S. PATENT DOCUMENTS

| | | | | |
|---|---|---|---|---|
| 5,110,727 | A | * | 5/1992 | Oberhardt ........... B01F 11/0045 422/110 |
| 2007/0286773 | A1 | * | 12/2007 | Schlautmann ... G01N 27/44791 422/68.1 |
| 2010/0297780 | A1 | * | 11/2010 | De Theije ........ G01N 33/54366 436/526 |

* cited by examiner

*Primary Examiner* — Christine T Mui
(74) *Attorney, Agent, or Firm* — NSIP Law

(57) ABSTRACT

A biochemical detection device with a controlled reaction incubation time includes a substrate; a probe disposed on the substrate; a dissolvable material layer disposed on the substrate, wherein the dissolvable material layer has a first opening defined therein, wherein the probe is received in the first opening; an absorbing material layer disposed on the dissolvable material layer and having a second opening defined therein, wherein the first opening communicates with the second opening and is smaller than the second opening; and a non-dissolvable material layer disposed on an inner face of the second opening of the absorbing material layer and on an exposed top face of the dissolvable material layer.

20 Claims, 7 Drawing Sheets

Negative control        1μM Hg$^{2+}$ added

BIOCHEMICAL DETECTION DEVICE WITH CONTROLLED REACTION INCUBATION TIME AND METHOD FOR PRODUCING THE SAME

CROSS-REFERENCE TO RELATED APPLICATION

This application claims a benefit under 35 U.S.C. § 119(a) of Korean Patent Application No. 10-2018-0022635 filed on Feb. 26, 2018, on the Korean Intellectual Property Office, the entire disclosure of which is incorporated herein by reference for all purposes.

BACKGROUND

1. Field

The present disclosure relates to a biochemical detection device with a controlled reaction incubation time, and to a method for producing the device. Further, the present disclosure relates to a sensor including the biochemical detection device with the controlled reaction incubation time.

2. Description of Related Art

A portable device based on a microfluidic element as a portable point-of-care detection device have been developed for easy use with minimizing user intervention. Typically, a target detection procedure includes a sample injection to a detected region, a reaction incubation, a sample removal, a washing and a detection. When the user involves each step in the overall detection process, an operation error may occur due to the involving of the user, which causes a reliability of a result of the point-of-care detection device to be lowered. Thus, there has been a need for minimizing the user intervention via automation by a passive mechanism inherent in the device.

In a conventional portable point-of-care detection device, a use of an immunochromatographic rapid test strip based on a porous paper structure is becoming popular, where when the user drops a liquid specimen onto the device, the liquid specimen is passively sucked into the device, thereby allowing for a very simple visual check of a qualitative detection result without a further intervention of the user. However, as an effort to develop a device capable of more accurate quantitative analysis with a higher detection sensitivity, a microfluidic element-based device has been studied which easily performs a quantitative analysis by treating a small amount of a reagent and a small amount of a sample precisely. However, more researches are needed for minimizing the user intervention via a passive control of a detection reaction time in order to solve a problem due to a complexity of a fully automated detection reaction device.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a portable point-of-care detection reaction device that minimizes the user intervention and reduces influence of the user and obtains a constant and accurate detection result via a passive control of a biochemical reaction time using an device-intrinsic passive mechanism.

In a first aspect of the present disclosure, there is provided a biochemical detection device with a controlled reaction incubation time, the device comprising: a substrate; a probe disposed on the substrate; a dissolvable material layer disposed on the substrate, wherein the dissolvable material layer has a first opening defined therein, wherein the probe is received in the first opening; an absorbing material layer disposed on the dissolvable material layer and having a second opening defined therein, wherein the first opening communicates with the second opening and is smaller than the second opening; and a non-dissolvable material layer disposed on an inner face of the second opening of the absorbing material layer and on an exposed top face of the dissolvable material layer, wherein a combination of the second opening and the first opening defines a reaction space, wherein when a liquid sample is injected into the reaction space, the dissolvable material layer is dissolved by the liquid sample, and, then, after a predetermined time, the liquid sample has been transferred to the absorbing material layer such that a reaction incubation time is terminated.

In one implementation of the first aspect, the device further comprises a cover disposed on the absorbing material layer.

In one implementation of the first aspect, the cover includes: an injection hole defined therein; and an injection flow channel defined therein to communicate between the injection hole and the reaction space.

In one implementation of the first aspect, when a washing is required, a washing solution is injected through the injection hole and then the washing solution passes through the injection flow channel to the reaction space to wash the probe.

In one implementation of the first aspect, a diameter of the second opening is greater than a diameter of the first opening.

In one implementation of the first aspect, the reaction incubation time is controlled by controlling a difference in size between the diameter of the second opening and the diameter of the first opening.

In one implementation of the first aspect, the reaction incubation time is adjusted based on a dissolution rate of the dissolvable material layer.

In a second aspect of the present disclosure, there is provided a method for manufacturing a biochemical detection device with a controlled reaction incubation time, the method comprising: preparing an absorbing material layer; forming a first opening in the absorbing material layer; attaching a dissolvable material layer onto a bottom of the absorbing material layer; bonding a non-dissolvable material layer to an inner face of the first opening of the absorbing material layer and to an exposed top face of the dissolvable material layer; forming a second opening defined in the dissolvable material layer and the non-dissolvable material layer, wherein the second opening is smaller than the first opening; and adhering a substrate having a probe attached thereto onto a bottom of the dissolvable material layer such that the probe is received in the second opening, wherein a combination of the second opening and the first opening defines a reaction space, wherein when a liquid sample is injected into the reaction space, the dissolvable material layer is dissolved by the liquid sample, and, then, after a predetermined time, the liquid sample has been transferred to the absorbing material layer such that a reaction incubation time is terminated.

In one implementation of the second aspect, the method further comprises disposing a cover on the absorbing material layer.

In one implementation of the second aspect, the cover includes: an injection hole defined therein; and an injection flow channel defined therein to communicate between the injection hole and the reaction space.

In one implementation of the second aspect, when a washing is required, a washing solution is injected through the injection hole and then the washing solution passes through the injection flow channel to the reaction space to wash the probe.

In one implementation of the second aspect, a diameter of the first opening is greater than a diameter of the second opening.

In one implementation of the second aspect, the reaction incubation time is controlled by controlling a difference in size between the diameter of the second opening and the diameter of the first opening.

In one implementation of the second aspect, the reaction incubation time is adjusted based on a dissolution rate of the dissolvable material layer.

In a third aspect of the present disclosure, there is provided a portable sensor including the biochemical detection device as defined above.

The present disclosure provides a portable point-of-care detection reaction device with a minimal user intervention, which has a high compatibility such that the device may be applied for a production of a portable biosensor platform.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

Figure 1:
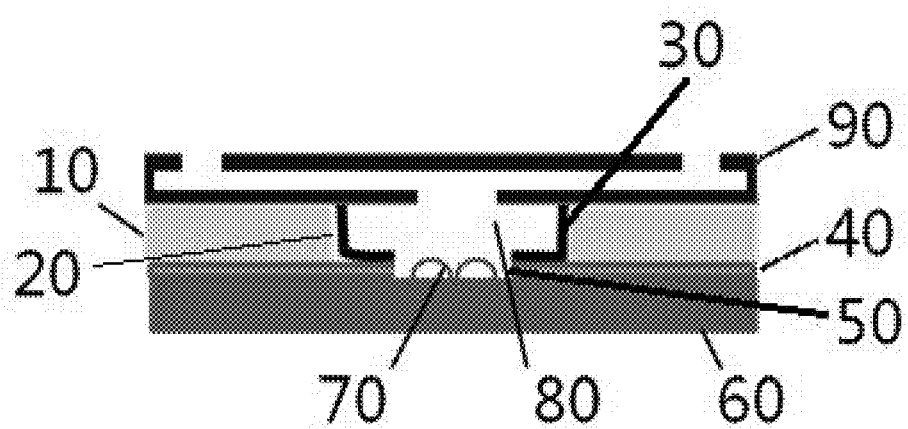
FIG. 1 shows a biochemical detection device with a controlled reaction incubation time according to one embodiment of the present disclosure.

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one or when preceding a list of" elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure".

The present disclosure is directed to a biochemical detection device in which a reaction incubation time required for a biomolecular reaction in a liquid-phase based point-of-care detection reaction device is passively controlled using a dissolvable material layer in a limited volume, thereby to minimize the user intervention.

According to the present disclosure, a liquid sample may be passively removed without an external force via dissolution and disintegration of a dissolvable material layer by the liquid sample in a certain time after an application of the sample in a limited volume of a reaction space. Thus, a conventional sequence of a sample injection into a detected region, a reaction incubation, a sample removal, a washing, and a detection may be changed to a new sequence of a sample injection into a detected region, a reaction incubation, a washing, and a detection. Thus, it may dispense with the sample removal step involving the user intervention.

In addition, a one-way shear flow may be generated even with a small amount of a washing solution through microfluidic channels formed via a disintegration and dissolution of the dissolvable material layer and through a absorbing material layer located outside a detected space. Thus, this may allow performing an immediate washing of a bottom of the detected space where capture probes are fixed. Further, in a subsequent adoption of a detection method that does not require washing, this may result in a simpler detection with a further reduction in the user intervention.

FIG. 1 shows a biochemical detection device with a controlled reaction incubation time according to one embodiment of the present disclosure.

A biochemical detection device with a controlled reaction incubation time according to one embodiment of the present disclosure includes a substrate 60; a probe 70 disposed on the substrate 60; a dissolvable material layer 40 disposed on the substrate 60, wherein the dissolvable material layer 40 has a first opening 50 defined therein, wherein the probe 70 is received in the first opening 50; an absorbing material layer 10 disposed on the dissolvable material layer 40 and having a second opening 20 defined therein, wherein the first opening 50 communicates with the second opening 20 and is smaller than the second opening 20; and a non-dissolvable material layer 30 disposed on an inner face of the second opening 20 of the absorbing material layer 10 and on an exposed top face of the dissolvable material layer 30.

The substrate 60 has the probe 70 disposed thereon. The probe 70 may be a capturing probe. The probe 70 may be conjugated with a detection probe as described below to form a complex. It is preferable that a size of the substrate is the same as a size of the absorbing material layer 10.

The dissolvable material layer 40 is disposed on the substrate 60 and has the first opening 50 defined therein. In this first opening 50, the probe 70 placed on the substrate may be received. Thus, the probe 70 may be received in a reaction space 80.

The dissolvable material layer 40 may be made of a material that is gradually dissolved and disintegrated by a liquid sample over time. The dissolution and disintegration of this dissolvable material layer may expose the absorbing material layer to the liquid sample. As a result, the liquid sample passively moves to the absorbing material layer and thus the reaction incubation time ends. In this case, the reaction incubation time may be adjusted based on a dissolution rate of the dissolvable material layer. Therefore, the reaction incubation time can be controlled by changing a material constituting the dissolvable material layer based on a reaction target substance.

The absorbing material layer 10 may act like an absorbent pad and may be disposed on the dissolvable material layer 40. The layer 10 has the second opening 20 defined therein having a size greater than that of the first opening 50 of the dissolvable material layer. The reaction space 80 may be defined by a combination of the second opening and the first opening.

The absorbing material layer 10 absorbs the liquid sample or washing solution. When a dissolution point of the dissolvable material layer reaches the absorbing material layer 10, the liquid sample moves to the absorbing material layer 10.

A diameter of the second opening 20 of the absorbing material layer 10 is greater than a diameter of the first opening 50 of the dissolvable material layer 40. This difference in size makes it possible to control the reaction incubation time. For example, when C1 is the diameter of the second opening 20, and the diameter of the first opening is C2, C1>C2. A change in the difference between the two diameters may be used to control a reaction incubation time between a probe and a target (ion, low molecular weight molecule, protein, bacteria, and cell, etc.). This will be discussed later with reference to FIG. 5.

The non-dissolvable material layer 30 is also referred to as an insoluble container layer. This layer 30 is disposed on an inner face of the second opening 20 of the absorbing material layer 10 and on an exposed top face of the dissolvable material layer 40 as shown in FIG. 1. The non-dissolvable material layer 30 may be made of a material that is not dissolvable by the liquid sample.

In the biochemical detection device with a controlled reaction incubation time in accordance with the present disclosure, when the liquid sample is injected into the reaction space 80, the dissolvable material layer 40 is dissolved by the liquid sample. Then, after a certain time, the liquid sample moves to the absorbing material layer 10 and thus the reaction incubation time is terminated.

In one example, a cover 90 may be additionally disposed on the absorbing material layer 10. A size of the cover 90 is preferably the same as a size of the absorbing material layer 10.

This cover 90 has an injection hole defined therein and an injection flow channel communicating between the injection hole and the reaction space 80.

When the washing is required, the washing solution is injected through the injection hole and the washing solution reaches the reaction space through the injection flow channel to wash the probe. Then, the washing solution moves, in a one-way manner, to the absorbing material layer 10 through micro channels formed in the dissolvable material layer 40 via the dissolution and disintegration of the dissolvable material layer 40. In this case, when a non-washing detection method is adopted, the process may shift to a signal detection operation immediately. When a washing operation is required, a small amount of washing liquid of several microliters is delivered to a central region of the device and then travels, only in a one-way manner, to the absorbing material layer as an outer portion of the device. Thus, the device may execute a convenient washing and then proceed to a signal detection operation.

The biochemical detection device with a controlled reaction incubation time according to one embodiment of the present disclosure has been exemplified. Hereinafter, a manufacturing method of the biochemical detection device with a controlled reaction incubation time will be exemplified. Repeated descriptions of the same portions therebetween will be omitted.

Figure 2:
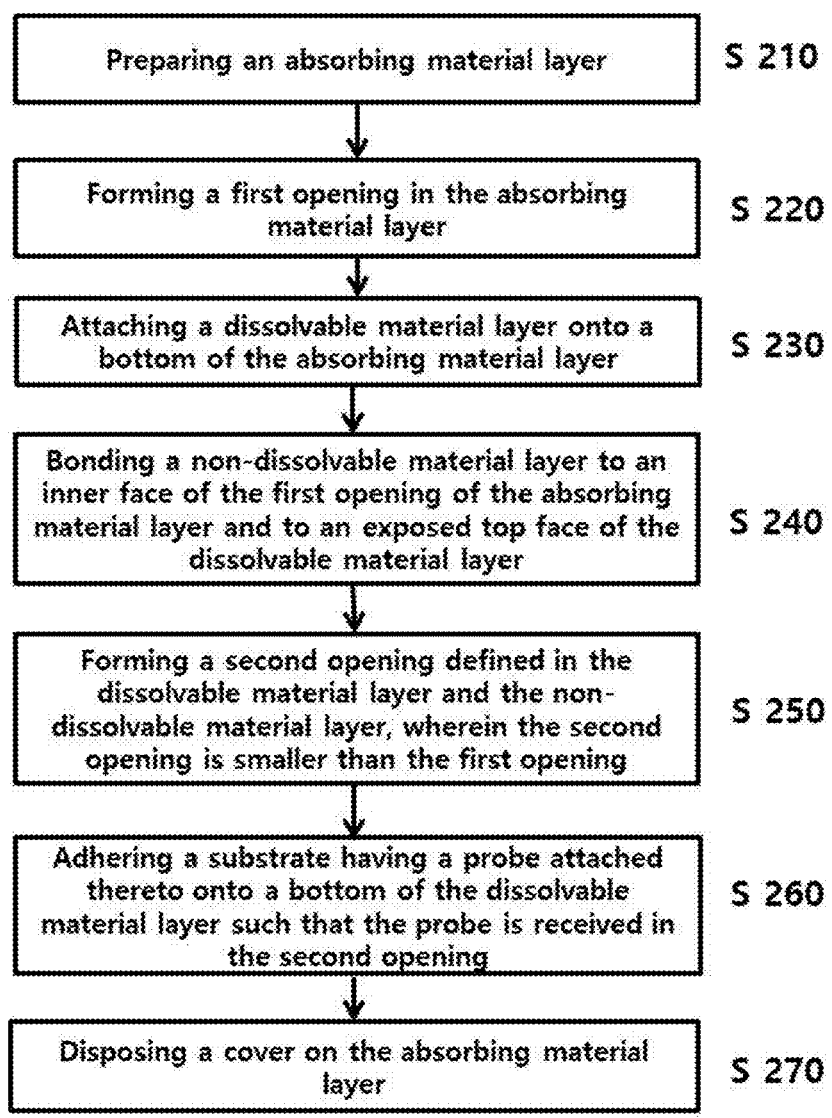
FIG. 2 shows a flow diagram of a method for manufacturing a biochemical detection device with a controlled reaction incubation time according to one embodiment of the present disclosure.
Figure 3:
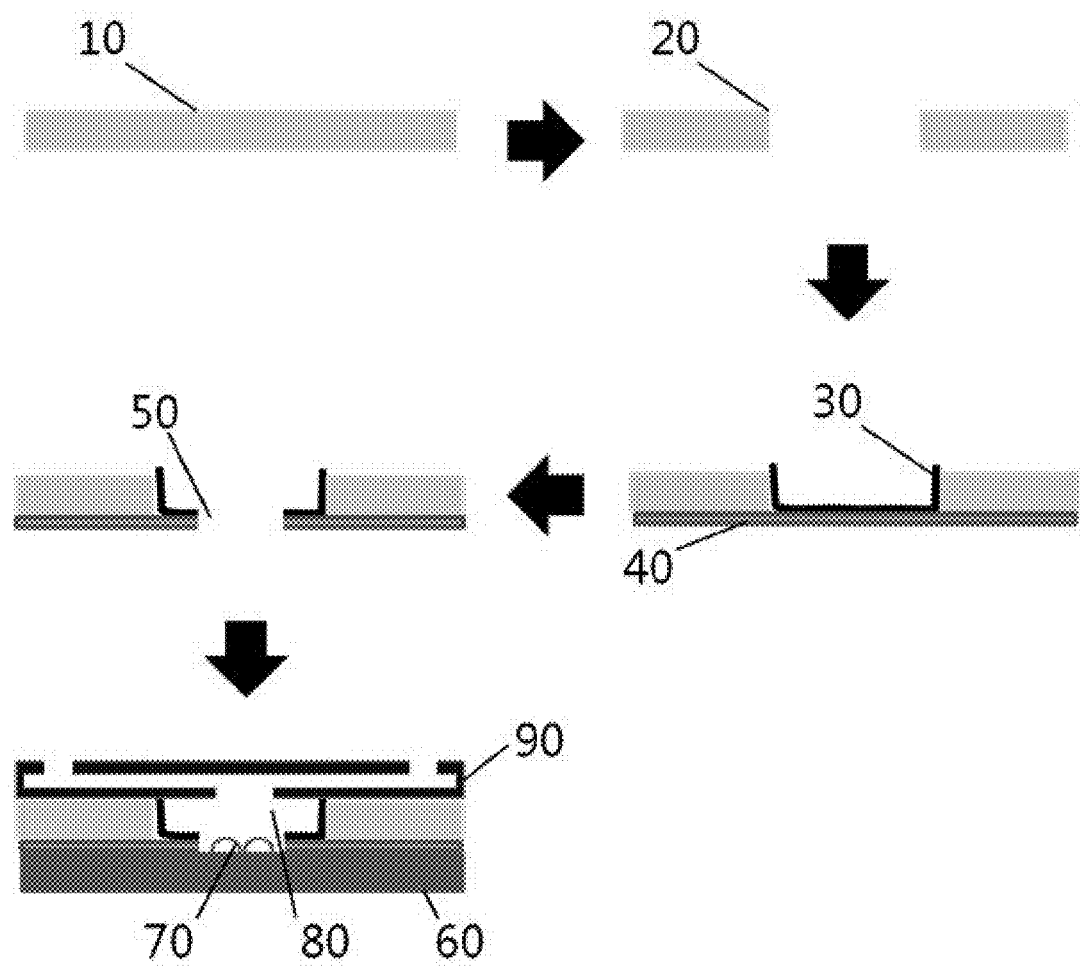
FIG. 3 shows a schematic diagram of a method for manufacturing a biochemical detection device with a controlled reaction incubation time according to one embodiment of the present disclosure.

FIG. 2 shows a flow diagram of a method for manufacturing a biochemical detection device with a controlled reaction incubation time according to one embodiment of the present disclosure. FIG. 3 shows a schematic diagram of a method for manufacturing a biochemical detection device with a controlled reaction incubation time according to one embodiment of the present disclosure.

A method for manufacturing a biochemical detection device with a controlled reaction incubation time according to one embodiment of the present disclosure includes an operation S 210 for preparing an absorbing material layer 10; an operation S 220 for forming a first opening 20 in the absorbing material layer 10; an operation S 230 for attaching a dissolvable material layer 40 onto a bottom of the absorbing material layer 10; an operation S 240 for bonding a non-dissolvable material layer 30 to an inner face of the first opening 20 of the absorbing material layer 10 and an exposed top face of the dissolvable material layer 40; an operation S 250 for forming a second opening 50 defined in the dissolvable material layer 40 and the non-dissolvable material layer 30, wherein the second opening 50 is smaller than the first opening 10; and an operation S 260 for adhering a substrate 60 having a probe 70 attached thereto onto a bottom of the dissolvable material layer 40 such that the probe 70 is received in the second opening 50.

In the S 210 operation, the absorbing material layer 10 is prepared. The absorbing material layer may act like an absorbent pad. A thickness thereof may be typically equal to or smaller than 2 mm. The absorbing material layer may have a square shape. A length thereof may be 2 to 3 cm. A shape and dimension thereof may vary widely depending on the sample or other conditions. A material of the absorbing material layer may include a paper, cotton, fabric, etc. The absorbing material layer may be embodied as a porous membrane.

In the S 220 operation, the first opening 20 is formed in the absorbing material layer 10. This first opening 20 may be circular in cross-section in FIG. 3, The diameter C1 of the first opening 20 may be smaller than or equal to 1 cm. This diameter may vary freely based on a amount of the sample or a purpose of use thereof.

In the S 230 operation, the dissolvable material layer 40 is attached to the bottom of the absorbing material layer 10. A thickness of the dissolvable material layer may be smaller than or equal to 0.5 mm. The thickness may freely vary according to a condition. The dissolvable material layer may be embodied as a water-soluble polymer film-based double-sided adhesive tape. In this connection, the water-soluble polymer may include poly vinyl alcohol (PVA), hydroxypropyl cellulose and pullulan.

In the S 240 operation, the non-dissolvable material layer 30 is bonded to an inner face of the first opening of the absorbing material layer 10 and to the exposed top face of the dissolvable material layer 40. This non-dissolvable material layer 30 is called an insoluble container layer. The non-dissolvable material layer may be embodied as a hydrophobic hydrocarbon complex-based film made of a wax of olefin molecular structure, or ethyl cellulose.

In the S 250 operation, a second opening 50 smaller than the first opening 20 is defined in the dissolvable material layer 40 and the non-dissolvable material layer 30. As shown in FIG. 3, the second opening 50 is formed by cutting a circular portion in the dissolvable material layer 40 and the non-dissolvable material layer 30. The diameter C2 of this second opening is smaller than the diameter C1 of the first opening. The reaction incubation time may be controlled by adjustment of the diameters C1 and C2.

In the S 260 operation, a substrate 60 having a probe 70 attached to a top of the substrate 60 is bonded to a bottom of the dissolvable material layer 40 so that the probe 70 is received in the second opening 50.

In this way, the reaction space 80 may be formed by combination of the second opening and first opening.

When the liquid sample is injected into the reaction space 80, the dissolvable material layer is dissolved by the liquid sample. After a certain time, the liquid sample moves to the absorbing material layer and thus the reaction incubation time is terminated.

Further, the S 270 operation may also include an operation to place a cover 90 on a top of the absorbing material layer.

This cover 90, as shown in FIG. 3 may have an injection hole; and an injection flow channel communicating between the injection hole and the reaction space.

When washing is required, the washing solution is injected through the injection hole and the washing solution reaches the reaction space through the injection flow channel to wash the probe.

Hereinafter, the present disclosure will be further exemplified along with specific examples.

Example 1

A rectangular shaped absorbing pad (absorbing material layer) was prepared and partially cut into a circular shape with a diameter C1 smaller than or equal to 1 cm. Thereafter, a water-soluble double-sided tape based on polyvinyl alcohol (PVA) serving as a dissolvable material layer at a thickness smaller than or equal to 0.5 mm was attached to a bottom of the absorbing pad. An olefinic film, which acts as a non-dissolvable material layer was bonded onto an inner face of the cut portion in the absorbing pad. A center region of each of the dissolvable material layer and the non-dissolvable material layer was cut into a circular shape with a diameter C2 smaller than C1.

Subsequently, a substrate having a probe attached thereto for capturing a target substance was aligned such that the probe position corresponds to the opening having the diameter C2. Then, the substrate was attached to the bottom of the dissolvable material layer so that the probe was exposed through the cutout of the C2 diameter size. In this way, the reaction space defined by the combination of the C1 and C2 diameter cuttings was defined in the center of the device. Further, the cover was disposed on the pad such that the injection flow channel and the injection hole communicate with the reaction space. The resulting structure is shown in FIG. 1.

The device of the present disclosure is advantageous in that it is easy to integrate a substrate with a signal amplification material or structure with a fluid control layer by separately designing the substrate onto which the detection probe is immobilized.

When the sample is injected, the dissolvable material layer located between the substrate and the insoluble container layer is gradually dissolved and disintegrated over time by the liquid sample while the sample flow stops in the reaction space. Once the dissolution and disintegration point is in contact with the absorptive pad located out of the reaction space, the liquid sample passively moves to the absorbing pad and, then immediately, the reaction incubation time is terminated.

In this connection, when a non-washing detection method is adopted, the process may shift to a signal detection operation immediately. When a washing operation is required, a small amount of washing liquid of several microliters is delivered to a central region of the device and then travels, only in a one-way manner, to the absorbing material layer as an outer portion of the device. Thus, the device may execute a convenient washing and then proceed to a signal detection operation. In the device in accordance with the present disclosure, a signal detection using fluorescence imaging or colorimetric method after the reaction of the target detected molecule may be employed.

Figure 4:
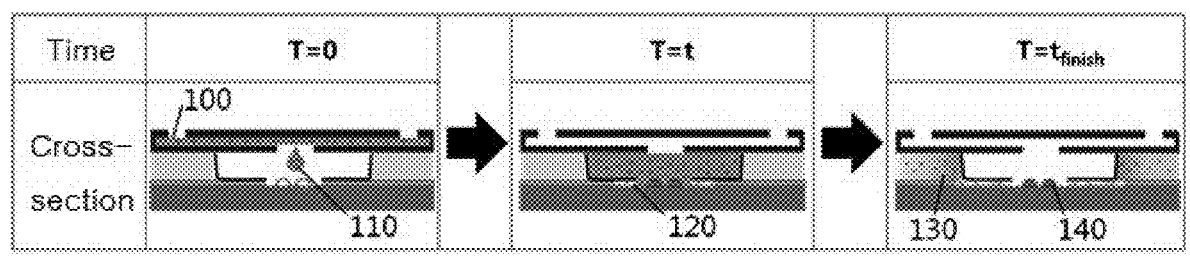
FIG. 4 shows a change in the device over time when a liquid sample is injected into the device according to one embodiment of the present disclosure.

FIG. 4 shows a change in the device over time when a liquid sample is injected into the device according to one embodiment of the present disclosure. When the liquid sample 100 is injected into the device of the present disclosure, dissolution and disintegration 120 of the dissolvable material layer gradually occurs at a time point t and proceeds toward the outer absorbent pad 10. Ultimately, when the dissolution and disintegration point meets the absorbent pad, the liquid sample immediately undergoes a passive suction 130 to the absorbent pad. We checked that the reaction incubation time for which a phosphor-based detection probe 110 conjugated with the target meets with the capturing probe 70 to form a complex 140 was terminated at $t_{finish}$.

Figure 5:
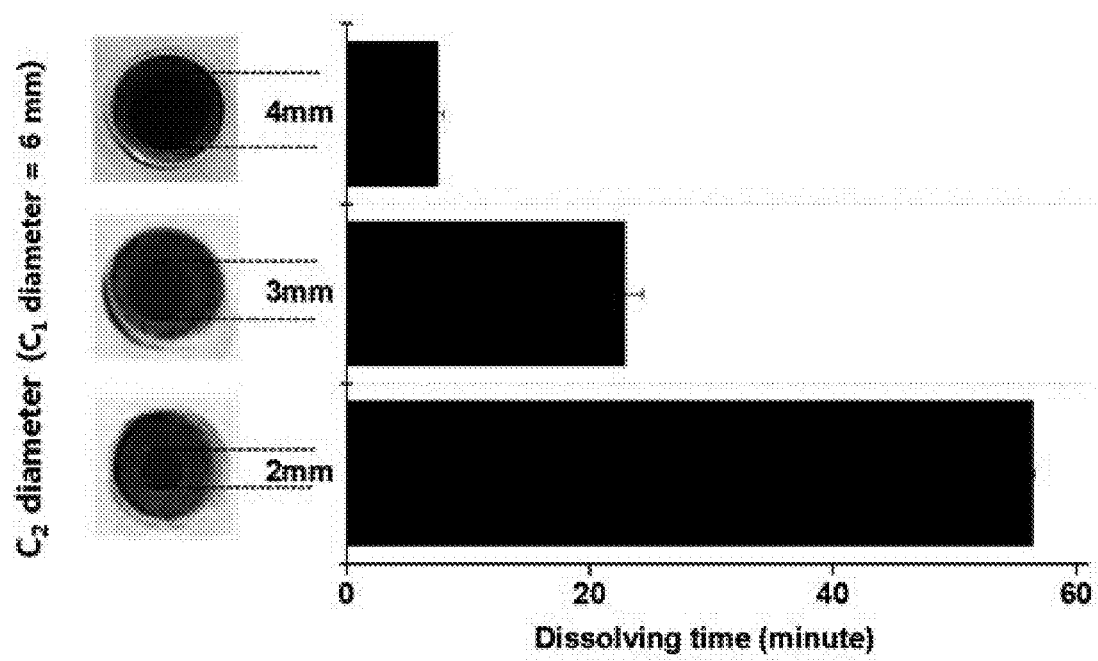
FIG. 5 shows a change in a termination time of a reaction incubation via adjusting a size of each of openings in the device in accordance with one embodiment of the present disclosure.

FIG. 5 shows a change in a termination time of a reaction incubation via adjusting a size of each of openings in the device in accordance with one embodiment of the present disclosure. As shown in FIG. 5, we checked that the diameters of the two openings C1 and C2 could be chosen to be different to optimize the reaction incubation termination time t to be adapted to a desired condition.

Figure 6:
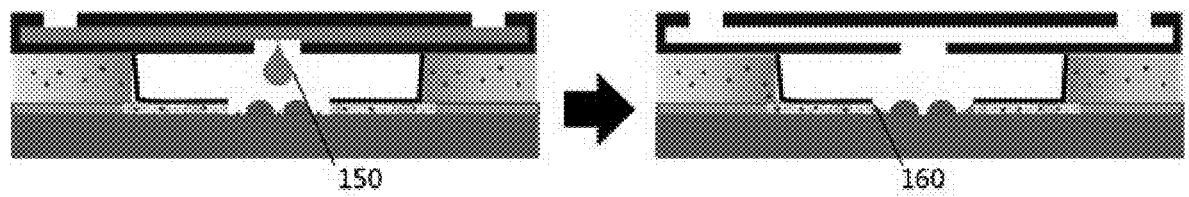
FIG. 6 shows an example state where cleaning is required in the device in accordance with one embodiment of the present disclosure.

FIG. 6 shows an example state where cleaning is required in the device in accordance with one embodiment of the present disclosure. As shown in FIG. 6, very easy washing can be realized when the detection method requiring the washing is adopted. After the termination of the reaction incubation time, the washing solution 150 was added. Thus, the washing solution is sucked, in a one-way manner, into the absorption pad through the fine flow channel formed in the dissolvable material layer 120 via the dissolution and disintegration thereof. In this way, a shear flow 160 is created to wash away an unreacted phosphor-bound detection probe (that is, the target is not conjugated thereto).

Figure 7:
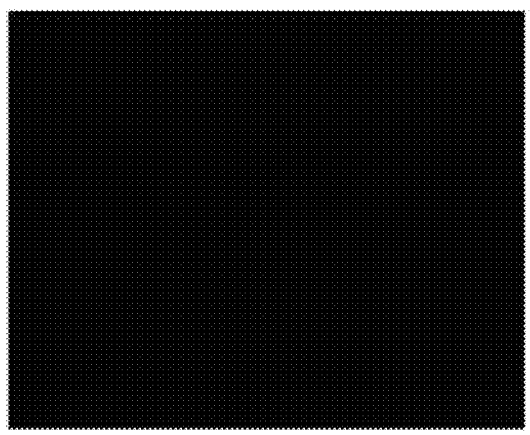
FIG. 7 shows an example of a verification for application of the device in accordance with one embodiment of the present disclosure.
Figure 7:
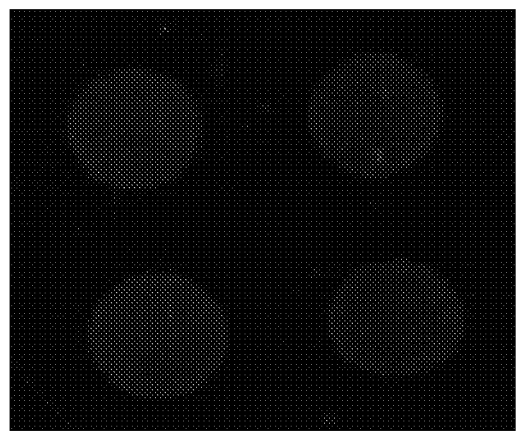

FIG. 7 shows an example of a verification for application of the device in accordance with one embodiment of the present disclosure. The capturing probe for capturing the heavy metal mercury ions was fixed to the sensor substrate. Then, a mixture between the red fluorescent quantum dot-coupled detection probe and mercury ions was injected into the reaction space receiving the capturing probe. The reaction incubation time has passively ended after about 30 minutes according to the principle of the present disclosure. After the washing, we imaged a fluorescence image and checked the detection signal.

The present disclosure provides a portable point-of-care detection reaction device with a minimal user intervention, which has a high compatibility such that the device may be applied for a production of a portable biosensor platform.

The description of the disclosed embodiments is provided to enable any person skilled in the art to make or use the present disclosure. Various modifications to these embodiments will be readily apparent to those skilled in the art of the present disclosure. The general principles defined herein may be applied to other embodiments without departing from the scope of the present disclosure. Thus, the present disclosure is not to be construed as limited to the embodiments set forth herein but rather to be accorded the widest scope consistent with the principles and novel features set forth herein.

What is claimed is:

1. A biochemical detection device with a controlled reaction incubation time, the device comprising:
   a substrate;
   a probe disposed on the substrate;
   a dissolvable material layer disposed on the substrate, wherein the dissolvable material layer has a first opening defined therein, and the probe is received in the first opening;
   an absorbing material layer disposed on the dissolvable material layer and having a second opening defined therein, wherein the first opening communicates with the second opening and is smaller than the second opening; and
   a non-dissolvable material layer disposed on an inner face of the second opening of the absorbing material layer and on an exposed top face of the dissolvable material layer,
   wherein a combination of the second opening and the first opening defines a reaction space, and
   wherein when a liquid sample is injected into the reaction space, the dissolvable material layer is dissolved by the liquid sample, and then, after a predetermined time, the liquid sample has been transferred to the absorbing material layer such that a reaction incubation time is terminated.

2. The biochemical detection device of claim 1, wherein the device further comprises a cover disposed on the absorbing material layer.

3. The biochemical detection device of claim 2, wherein the cover includes:
   an injection hole defined therein; and
   an injection flow channel defined therein to communicate between the injection hole and the reaction space.

4. The biochemical detection device of claim 3, wherein when a washing is required, a washing solution is injected through the injection hole and then the washing solution passes through the injection flow channel to the reaction space to wash the probe.

5. The biochemical detection device of claim 1, wherein a diameter of the second opening is greater than a diameter of the first opening.

6. The biochemical detection device of claim 5, wherein the reaction incubation time is controlled by controlling a difference in size between the diameter of the second opening and the diameter of the first opening.

7. The biochemical detection device of claim 1, wherein the reaction incubation time is adjusted based on a dissolution rate of the dissolvable material layer.

8. A method for manufacturing a biochemical detection device with a controlled reaction incubation time, the method comprising:
preparing an absorbing material layer;
forming a first opening in the absorbing material layer;
attaching a dissolvable material layer onto a bottom of the absorbing material layer;
bonding a non-dissolvable material layer to an inner face of the first opening of the absorbing material layer and to an exposed top face of the dissolvable material layer;
forming a second opening defined in the dissolvable material layer and the non-dissolvable material layer, wherein the second opening is smaller than the first opening; and
adhering a substrate having a probe attached thereto onto a bottom of the dissolvable material layer such that the probe is received in the second opening,
wherein a combination of the second opening and the first opening defines a reaction space, and
wherein when a liquid sample is injected into the reaction space, the dissolvable material layer is dissolved by the liquid sample, and then, after a predetermined time, the liquid sample has been transferred to the absorbing material layer such that a reaction incubation time is terminated.

9. The method of claim 8, wherein the method further comprises disposing a cover on the absorbing material layer.

10. The method of claim 9, wherein the cover includes:
an injection hole defined therein; and
an injection flow channel defined therein to communicate between the injection hole and the reaction space.

11. The method of claim 10, wherein when a washing is required, a washing solution is injected through the injection hole and then the washing solution passes through the injection flow channel to the reaction space to wash the probe.

12. The method of claim 8, wherein a diameter of the first opening is greater than a diameter of the second opening.

13. The method of claim 12, wherein the reaction incubation time is controlled by controlling a difference in size between the diameter of the second opening and the diameter of the first opening.

14. The method of claim 8, wherein the reaction incubation time is adjusted based on a dissolution rate of the dissolvable material layer.

15. A portable sensor including the biochemical detection device according to claim 1.

16. A portable sensor including the biochemical detection device according to claim 2.

17. A portable sensor including the biochemical detection device according to claim 3.

18. A portable sensor including the biochemical detection device according to claim 4.

19. A portable sensor including the biochemical detection device according to claim 5.

20. A portable sensor including the biochemical detection device according to claim 6.

* * * * *